US008597247B2

(12) United States Patent
Peterson et al.

(10) Patent No.: US 8,597,247 B2
(45) Date of Patent: Dec. 3, 2013

(54) TUBE BRACKET FOR FLUID APPARATUS

(75) Inventors: Thomas Lloyd Peterson, Eden Prairie, MN (US); Thomas John McPeak, Shakopee, MN (US)

(73) Assignee: Nestec S.A., Vevey (CH)

( * ) Notice: Subject to any disclaimer, the term of this patent is extended or adjusted under 35 U.S.C. 154(b) by 260 days.

(21) Appl. No.: 12/991,803

(22) PCT Filed: Sep. 19, 2008

(86) PCT No.: PCT/US2008/076983
§ 371 (c)(1),
(2), (4) Date: Jan. 31, 2011

(87) PCT Pub. No.: WO2009/145779
PCT Pub. Date: Dec. 3, 2009

(65) Prior Publication Data
US 2011/0270213 A1      Nov. 3, 2011

Related U.S. Application Data

(60) Provisional application No. 61/057,791, filed on May 30, 2008.

(51) Int. Cl.
*A61M 1/00*       (2006.01)
(52) U.S. Cl.
USPC ....................................................... 604/151
(58) Field of Classification Search
USPC ........................................ 604/151, 408, 910
See application file for complete search history.

(56) References Cited

U.S. PATENT DOCUMENTS

| 4,515,535 | A |   | 5/1985  | D'Silva              |
|-----------|---|---|---------|----------------------|
| 5,634,907 | A | * | 6/1997  | Rani et al. ..... 604/151 |
| 5,681,294 | A |   | 10/1997 | Osborne et al.       |
| 7,129,366 | B2 |  | 10/2006 | Yang                 |
| 7,160,087 | B2 |  | 1/2007  | Fathallah et al.     |
| 7,758,551 | B2 |  | 7/2010  | Wiesner et al.       |

FOREIGN PATENT DOCUMENTS

| EP | 0306458     | * | 2/1988 |
|----|-------------|---|--------|
| EP | 1829574     |   | 9/2007 |
| GB | 2351523     |   | 1/2001 |
| JP | 20011515369 |   | 9/2001 |
| JP | 2005507869  |   | 3/2005 |
| JP | 2007505701  |   | 3/2007 |
| JP | 2007236934  |   | 9/2007 |

* cited by examiner

*Primary Examiner* — Kevin C Sirmons
*Assistant Examiner* — Deanna K Hall
(74) *Attorney, Agent, or Firm* — K&L Gates LLP

(57) ABSTRACT

A bracket is provided. In an embodiment, the bracket comprises a first seat and a second seat. The first seat is sized to retain a first fluid implement. The second seat is sized to retain a second fluid implement from the bracket. The second seat includes a top opening, a side opening and a front concave portion. The second seat is configured to prevent inadvertent removal of the second fluid implement from the bracket. A fluid delivery apparatus including the bracket, as well as a method for delivering fluid, such as medical fluids including nutritional fluids, and industrial fluids through the delivery apparatus is also provided.

15 Claims, 5 Drawing Sheets

TUBE BRACKET FOR FLUID APPARATUS

BACKGROUND

The present disclosure relates generally to a fluid delivery apparatus, and especially a medication delivery apparatus.

A fluid delivery apparatus generally includes a pump mechanism for delivering a predetermined volume of fluid at a specific flow rate from a fluid source to a receptacle, in an open or closed environment. To deliver the requisite volume of fluid at a consistent and/or predetermined flow rate, the pump mechanism is usually between the fluid source and the receptacle, and the fluid source and receptacle are in fluid communication with the pump mechanism. One type of a fluid delivery apparatus is a medication delivery apparatus generally includes a pump mechanism for delivering a predetermined volume of medication at a specific flow rate from a medication source to a patient. To deliver the requisite volume of medication at a consistent flow rate, the pump mechanism is usually between the medication source and the patient, and the medication source and patient are in fluid communication with the pump mechanism.

A medication delivery apparatus can use many different kinds of pumps to deliver medication. A common pump in delivery apparatus is the peristaltic pump, which is a type of positive displacement pump used for pumping a variety of fluids. The fluid is contained generally within a flexible tube fitted around a rotor. The rotor, having a number of "rollers", "shoes" or "wipers" attached to the external portion of the pump, compresses the flexible tube. As the rotor turns, the part of tube under compression closes (or "occludes"), thus forcing the fluid to move through the tube. Moreover, as the tube opens to its natural state after compression, fluid flow is induced to the pump. This repeated action pumps fluid through the delivery apparatus and to the patient.

To place the flexible tube under the requisite pressure to allow a pump, such as the peristaltic pump, to work properly, tubing on both sides of the pump must be taut. This generally requires retaining the tubing on both sides of the pump such that the tubing remains taut through the pump. Such a retaining means can include, for example, a bracket, clamp, or valve. As long as the flexible tubing stays taut through the pump, any predetermined values provided for the delivery apparatus (e.g. delivery time, rate, volume, etc.) can be measured by the delivery apparatus and maintained by the pump.

However, with existing delivery apparatuses, current designs of retaining means, such as a bracket, quite frequently allow for tubing to detach from the bracket. Detachment can occur in many ways such as, for example, excessive movement by a patient causing the tubing to be pulled off the bracket or inadvertent detachment by a user (e.g. a caregiver or medical personnel).

When detachment occurs, freeing the flexible tubing from pump retention, free flow may result. At free flow, medication will flow freely through the delivery apparatus from the source to the patient without control from the delivery apparatus and associated pump. This can result in an over-delivery of medication to a patient, thus serving as a health hazard depending on the type of patient condition, the type of medication and the availability of medical personnel at the time of free flow. Furthermore, even if the delivery apparatus has an alarm that triggers upon tubing detachment or disconnection, many delivery apparatuses cannot prevent free flow of medication because the flow of medication acts independent of the delivery apparatus (e.g. gravity flow).

SUMMARY

The present disclosure relates generally to delivery of fluid to a receptacle. More specifically, the present disclosure relates to a medication delivery system and methods for delivering medication to a patient using the system.

In an embodiment, the present disclosure provides a bracket comprising a first seat and a second seat. The first seat is sized to retain a first medical implement. The second seat is sized to retain a second medical implement. The second seat includes a top opening, a side opening and a front concave portion. The second seat is configured to prevent inadvertent removal of the second medical implement from the bracket. The bracket may be affixed to a medication delivery apparatus.

In an embodiment, the top opening is sized to allow insertion of the second medical implement into the second seat.

In an embodiment, the front concave portion is sized and shaped to allow angled insertion of the second medical implement into the second seat.

In an embodiment, the second medical implement further includes a tube extending downward from the second medical implement. The tube may connect the first medical implement to the second medical implement.

In an embodiment, the side opening is sized to allow insertion of the tube into the second seat.

In an embodiment, the first seat includes an upper opening sized to allow insertion of the first medical implement into the first seat. The first seat may be tapered towards a bottom opening of the first seat to retain the first medical implement in the first seat.

In another embodiment, the present disclosure provides a medication delivery apparatus. The medication delivery apparatus comprises a housing and a tube. The housing includes a pump and a bracket. The bracket includes a first seat and a second seat. The first seat is sized to retain a first medical implement. The second seat is sized to retain a second medical implement disposed between the first medical implement and a patient. The second seat is configured to prevent inadvertent removal of the second medical implement from the bracket. The tube passes through the second medical implement, providing fluid communication between the first medical implement and the patient.

In an embodiment, the second seat includes a top opening sized to allow insertion of the second medical implement into the second seat.

In an embodiment, the second seat includes a front concave portion sized and shaped to allow angled insertion of the second medical implement into the second seat.

In an embodiment, the second seat includes a side opening sized to allow insertion of the tube into the second seat.

In an embodiment, the pump is disposed between the first medical implement and the second medical implement. Further, the pump may connect to the tube and operate to pump medication from the first medical implement to the second medical implement. Even further, the pump may be a peristaltic pump.

In an embodiment, the housing further includes a tube guide formed above the second seat and sized to retain a portion of the tube extending from the second medical implement to the patient.

In yet another embodiment, a method for delivery medication is provided. The method comprises providing a delivery apparatus comprising a pump and a bracket comprising a first seat and a second seat. A first medical implement is placed in the first seat. A tube, which connects the first medical implement to a second medical implement, is placed in communication with the pump. The method also includes inserting a portion of the tube adjacent the second medical implement through a side opening of the second seat. The method further includes inserting the second medical implement at an angle through a front concave opening of the second seat, wherein the second seat is configured to prevent inadvertent removal of the second medical implement from the second seat. The method also includes attaching the delivery apparatus to a patient, and delivering medication to the patient.

In an embodiment, the method for delivery medication further includes inserting at least a portion of the tube between the second medical and the patient implement into a tube guide provided above the second seat.

In an embodiment, the tube has a smaller width or diameter than the second medical implement. The side opening may be sized to permit insertion and removal of the tube. Alternatively, the side opening is sized to prevent insertion and removal of the second medical implement.

It is an advantage of the present disclosure to provide a bracket that retains multiple medical implements on the delivery system It is an advantage of the present disclosure to provide a bracket that retains multiple medical implements in fluid communication with a pump.

It is an advantage of the present disclosure to provide a medication delivery apparatus that retains a tube set on the delivery apparatus.

It is an advantage of the present disclosure to provide a medication delivery apparatus that retains a tube set on a pump.

It is another advantage of the present disclosure to provide a bracket that prevents inadvertent disconnection of a tube set from the bracket.

It is another advantage of the present disclosure to provide a bracket that prevents inadvertent disconnection of a tube set from a pump.

It is a further advantage of the present disclosure to provide an improved method for delivering medication from a fluid source to a patient.

It is a further advantage of the present disclosure to provide an improved method for retaining a medical implement on a bracket of a delivery apparatus.

It is yet another advantage of the present disclosure to provide an improved method for retaining medical tubing on a pump.

Additional features and advantages are described herein, and will be apparent from the following Detailed Description and the figures.

DETAILED DESCRIPTION

Figure 1:
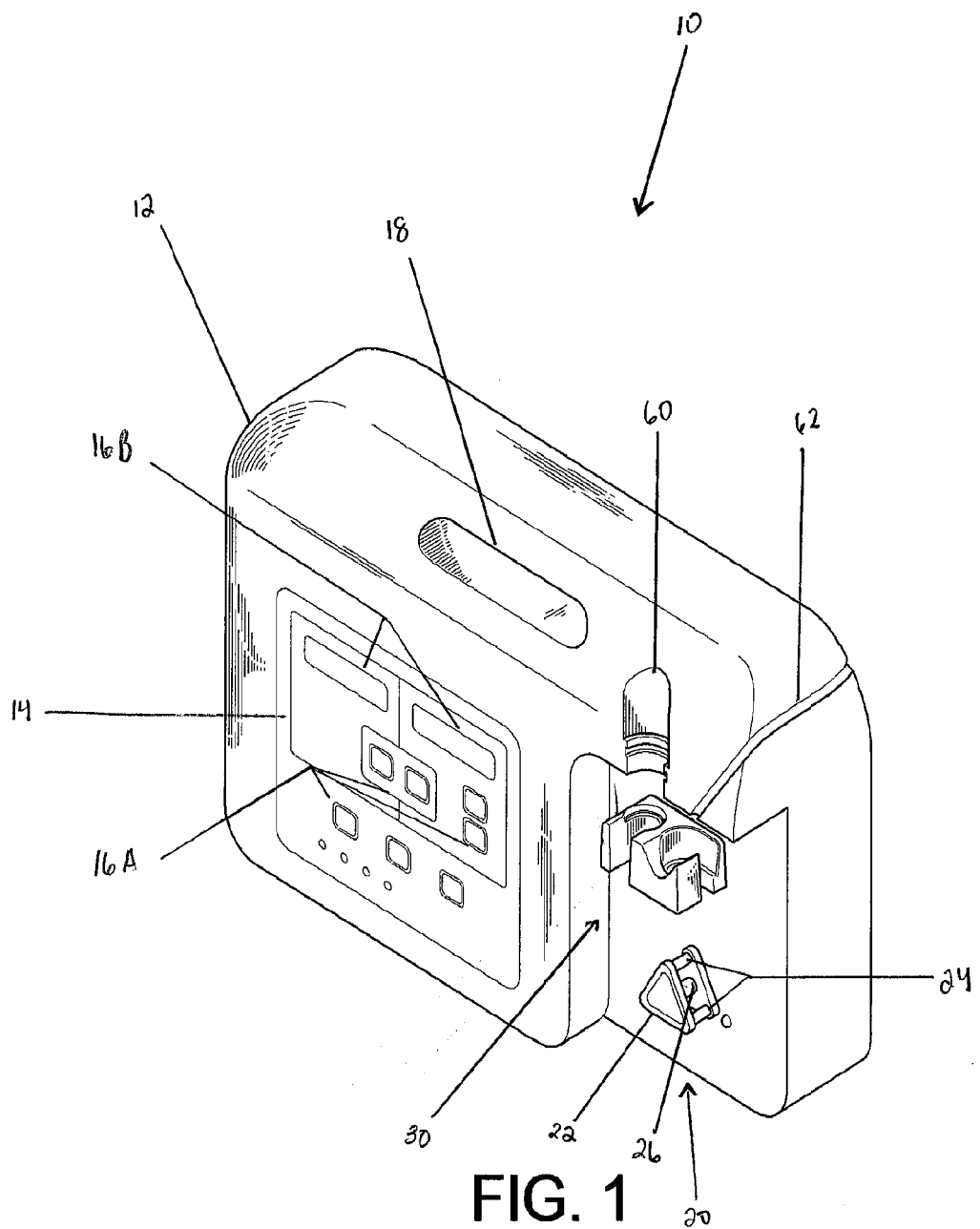
FIG. 1 is a perspective view of one embodiment of a medical delivery system of the present disclosure.

A fluid delivery apparatus generally includes a pump mechanism for delivering a predetermined volume of fluid at a predetermined flow rate from a fluid source to a receptacle, in an open or closed environment. To deliver the requisite volume of fluid at a consistent and/or predetermined flow rate, the pump mechanism is usually between the fluid source and the receptacle, and the fluid source and receptacle are in fluid communication with the pump mechanism. One type of a fluid delivery apparatus is a medication delivery apparatus generally includes a pump mechanism for delivering a predetermined volume of medication at a specific flow rate from a medication source to a patient. To deliver the requisite volume of medication at a consistent flow rate, the pump mechanism is usually between the medication source and the patient, and the medication source and patient are in fluid communication with the pump mechanism.

The following definitions may contain examples that are meant as illustrations and intended to be non-limiting to the scope of the invention.

As used in herein medicine, medicinal, and words of similar root origin includes intravenous fluids, nutritional fluids, dermatologic fluids and those fluids that would be understood by those of ordinary skill in the art as providing nutrition, or treatment or prevention of a disease or condition, by any means, including topically, intravenous, intramuscular, or through the gastro-intestinal tract.

As used in herein fluid shall include liquids, gels, and other non solids and non-gasses that would be understood by those of ordinary skill in the art to be capable of flowing, including medical fluids and industrial fluids.

As used in herein medicinal fluid include those fluids that would be understood by those of ordinary skill in the art, as providing nutrition, or treatment or prevention of a disease or condition, be by any means, including topically, intravenous, intramuscular, or through the gastro-intestinal tract.

As used in herein nutritional fluid include those fluids that would be understood by those of ordinary skill in the art, as providing nutrition, or treatment or prevention of a disease or condition through nutritional intervention, through the gastro-intestinal tract. Nutritional fluids are also intended to include complete nutritionals (i.e. those that provide sufficient nutrients and energy to sustain life), non-complete nutritionals (those that provide at least one, but not all, nutrients and energy to sustain life), beverages, thickeners, flavorings including sweeteners, and colorants, and those delivered through a dispensing device into a cup or other suitable receptacle.

As used in herein tube feeding formula include those nutritional fluids that would be understood by those of ordinary skill in the art to be delivered to a patient through the gastro-intestinal tract by way of a tube through the mouth, nose, port or other acceptable means.

As used in herein specialized tube feeding formula include those tube feeding formulas that would be understood by those of ordinary skill in the art, to provide benefits beyond or in addition to a standard tube feed formula, for example, a formula for a patient with diabetes, a renal disorder, gastrointestinal disorder (i.e. an elemental or semi-elemental formula) or a pulmonary disorder, or those formula used in a critical care or surgical situation to provide wound healing or immunologic support over and above a standard tube feeding formula.

As used in herein industrial fluid include those fluids that would be understood by those of ordinary skill in the art to be anything but a medicinal fluid, including: lubricants, fuels, cleaners, deodorizers, hydrating, thickeners, thinners, insect control, pest control, colorants, and the like.

As used herein patient shall include any animal, including a human.

As used herein animal include, but is not limited to fish, amphibians, reptile, avians and mammals which includes humans.

As used herein mammal includes but is not limited to rodents (murine), aquatic mammals, domestic animals such as canines, lupines, rabbits and felines, farm animals such as sheep (ovine), pigs (porcine), cows (bovines), goats (hircrine) and horses (equine), and humans.

Wherein the term mammal is used, it is contemplated that it also applies to other animals that are capable of the effect exhibited or intended to be exhibited by the mammal.

Wherein the terms animal or mammal or their plurals are used, it is contemplated that it also applies to any animals that are capable of the effect exhibited or intended to be exhibited by the context of the passage.

Although a medical delivery device is described below the scope of the present invention is intended to include any device that can deliver a fluid from any source, through a pumping mechanism to a suitable receptacle, be it living, mechanical, natural or artificial. The parts of the medical delivery device described below are intended to include parts of any fluid or nutritional delivery device that provide the same or similar structure and/or function and would work with the bracket of the present invention.

Referring to the Figures generally, where like reference numerals denote like structure and elements, and in particular to FIG. 1, a perspective view of an embodiment of a medical delivery apparatus 10 is shown, which functions to deliver a controlled and consistent level of medication to a patient. The delivery apparatus 10 can be free standing, held by a user or attached to a pole via a pole clamp (not shown) on the backside of the delivery apparatus 10. The delivery apparatus 10 may be powered by a standard power cord or be a cordless system with associated battery charging capabilities. Alternatively the pump maybe powered by a mechanical means, such as a crank that directly powers the pump or through a mechanism that stores and/or rations the mechanical energy for later use (such as in a non-battery powered watch). The delivery apparatus 10 may also have an alarm that sounds when the delivery apparatus 10 malfunctions. Malfunctions may include, for example, disconnection from the patient, disconnection from the medication source, disconnection from the delivery mechanism (e.g. pump), or interrupted or clogged medication flow through the deliver apparatus 10.

The delivery apparatus 10 includes a housing 12. The housing 12 includes a data input screen 14, a handle 18, a pump 20, a bracket 30, a relief space 60, and a tubing guide 62. The housing 12 is made of acrylonitrile butadiene styrene ("ABS"), but can be made of any other rigid plastic.

The data input screen 14, as illustrated in the embodiment of FIG. 1, includes a plurality of control buttons 16A and a plurality of displays 16B for controlling flow of medication through delivery apparatus 10. Each control button 16A generally will serve a specific function such as, for example, turning the delivery apparatus 10 on and/or off, starting and/or stopping operation of the delivery apparatus 10, setting a dose limit, resetting display values, increasing flow rate or decreasing flow rate. Each display 16B also will serve a specific function such as, for example, displaying delivery flow rate of medication or displaying total volume of medication delivered.

The pump 20, as illustrated in the embodiment of FIG. 1, is a peristaltic pump that includes a pump casing 22, a plurality of contact pegs 24 and a rotation means 26. Pump casing 22 covers the internal mechanism of pump 20. The contact pegs 24, as will be discussed below, exert pressure on a tube retained against the contact pegs 24. The rotation means 26 rotates the pump 20 to compress the tube to close (or "occlude") the tube, thus forcing the medical fluid to move through the tube. Moreover, as the tube opens to its natural state after compression, fluid flow is induced to the pump 20. This repeated action pumps medical fluid through the delivery apparatus 10 and to the patient. The pump 20 and all its components are made of ABS, but can be made of any other rigid plastic.

Figure 2:
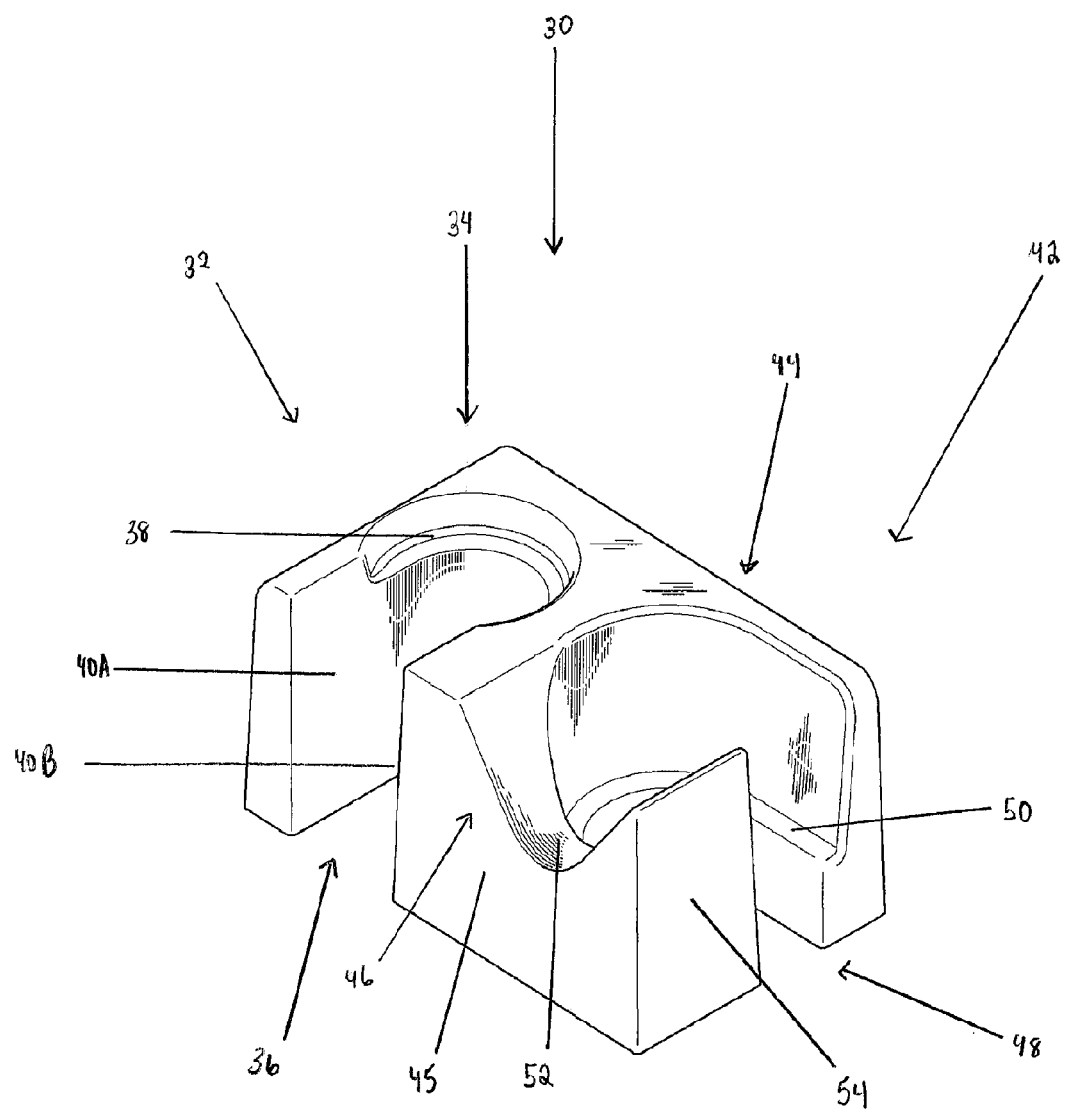
FIG. 2 is a perspective view of one embodiment of a bracket of the present disclosure.
Figure 3A:
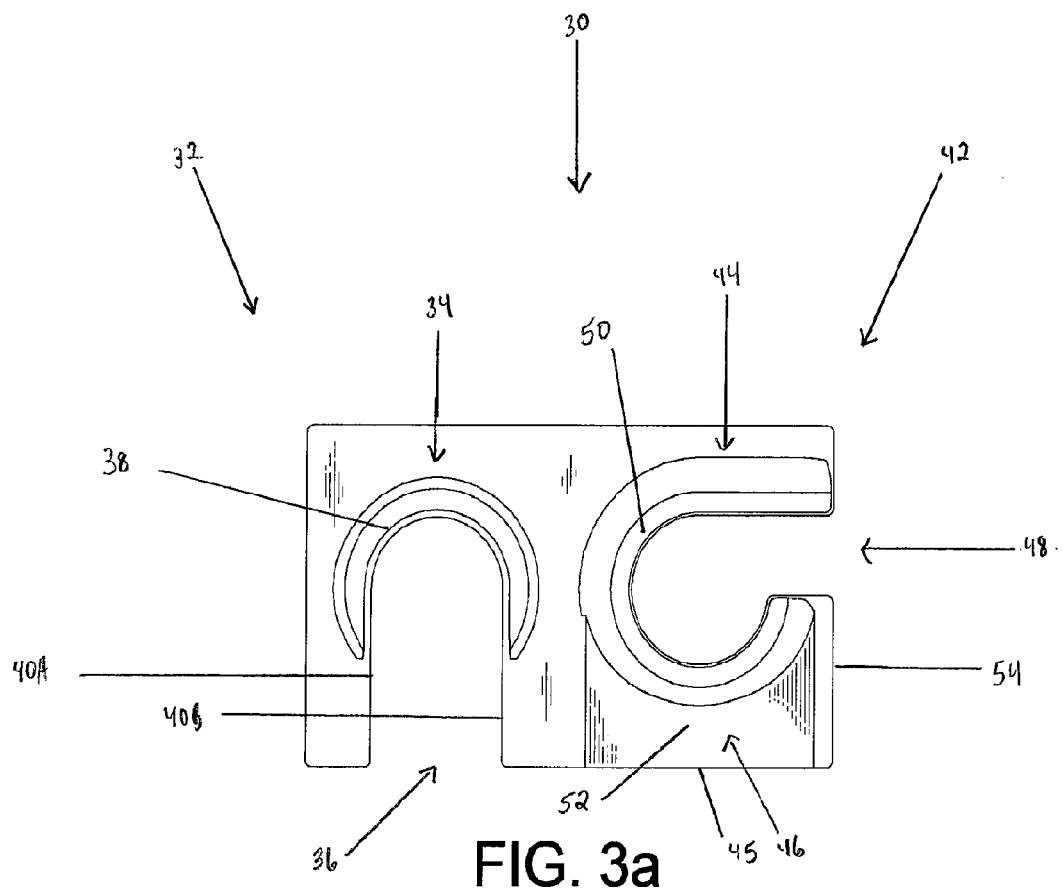
FIG. 3a is a top view of the bracket embodiment of FIG. 2.
Figure 3B:
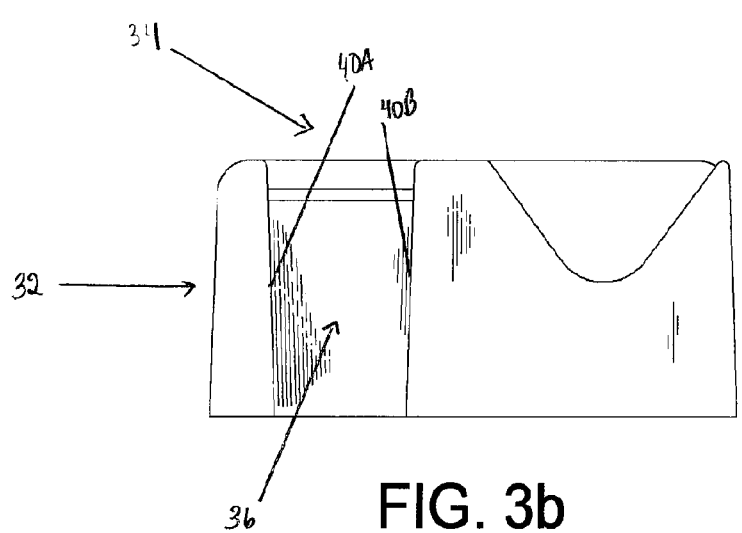
FIG. 3b is a front view of the bracket embodiment of FIG. 2.

As illustrated in FIG. 2, the bracket 30, also made of ABS or any other rigid plastic, includes a first seat 32 and a second seat 42. The first seat 32 includes a first top opening 34 below relief space 60, a front opening 36, a first seat ledge 38, and interior surfaces 40A and 40B. The first seat ledge 38 forms near the first top opening 34 in FIG. 2, but may be formed anywhere along the second seat 42 as needed. As illustrated in FIG. 3a, the first top opening 34 and the front opening 36 of the first seat 32 have substantially the same widths. Alternatively, as illustrated in FIG. 3b, the interior surfaces 40A and 40B taper from the top to the bottom of the first seat 32 such that the width at the bottom of the first seat 32 is less that the width of the top of the first seat 32, namely the first top opening 34 and the top of the front opening 36.

The second seat 42 includes a second top opening 44 below tubing guide 62, a front wall 45 having a concave opening 46, a side opening 48, a second seat ledge 50, a concave center surface 52 partially defining the concave opening 46, and a side wall 54. The second seat ledge 50 forms near the bottom of the second seat 42 in FIG. 2, but may be formed anywhere along the second seat 42 as needed. Further, as illustrated in FIG. 3a, the side wall 54 of the second seat 42 has a greater width than the concave center surface 52 of the second seat 42. Because of the width of the side wall 54, the side opening 48 on the second seat 42 has a lesser width than the second top opening 44 and the concave opening 46 on the front wall 45.

As will be described in detail below, the first seat 32 functions to retain a first medical implement on the bracket 30 and the second seat 42 functions to retain a second medical implement on the bracket 30 and prevent inadvertent detachment of the second medical implement from the second seat 34.

Figure 4A:
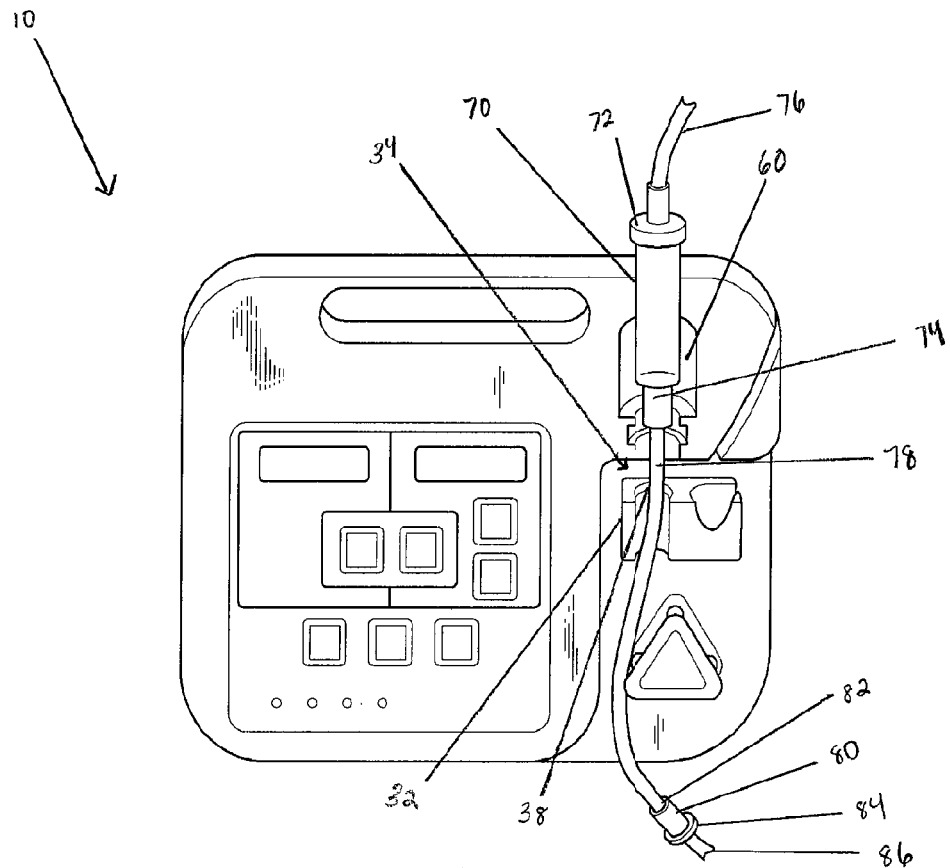
FIG. 4a-4d are front views illustrating the insertion of the first and second medical implements into the bracket according to one embodiment of the present disclosure.

Referring now to FIG. 4a, to prepare delivery apparatus 10 for delivering medication from a fluid source to a patient, a user first affixes a first medical implement 70 onto the first seat 32 of the bracket 30. To affix properly the first medical implement 70, a user moves the first medical implement 70 downward through the relief space 60 and through the first top opening 34. The user continues to move the first medical implement 70 through the first seat 32 until it comes to rest on the first seat ledge 38. The first seat ledge 38 prevents the first medical implement 70 from passing through the first seat 32 without being retained within the seat.

Alternatively, the tapered interior walls 40A and 40B, best illustrated in FIG. 3b, can taper to a width that also prevents the first medical implement from passing through the first seat 32 without being retained within the seat. In this embodiment, the first medical implement 70 slip-fits into the first seat 32 about the narrower, bottom portion of the interior walls 40A and 40B.

The first medical implement 70, as illustrated in the embodiment of FIG. 4a, is a drip chamber including a first chamber end 72 and a second chamber end 74. The first chamber end 72 attaches to a first plastic tubing 76 that places the first medical implement 70 in fluid communication with a medication source (not shown). Besides a drip chamber, the first medical implement 70 may be any medical device capable of transferring medication and sized to fit and be retained within the first seat 32.

As further illustrated in the embodiment of FIG. 4a, the second chamber end 74 attaches to silicone tubing 78 that places the first medical implement 70 in fluid communication with a second medical implement 80. The second medical implement is generally a pump adapter having a first adapter end 82 that connects with the silicone tubing 78, and a second adapter end 84 that connects with a second plastic tubing 86. The second plastic tubing 86 places the second medical implement 80 in fluid communication with the patient (not shown), or the patient's feeding tube (not shown).

The first medical implement 70, or drip chamber of FIG. 4a, can be made, for example, from polyvinyl chloride ("PVC") or any similar rigid plastic material. Likewise, the second medical implement 80, or pump adapter of FIG. 4a, can be made, for example, from PVC or any similar rigid plastic material. Further, the first and second plastic tubing 76 and 86 generally is non-rigid PVC.

Figure 4B:
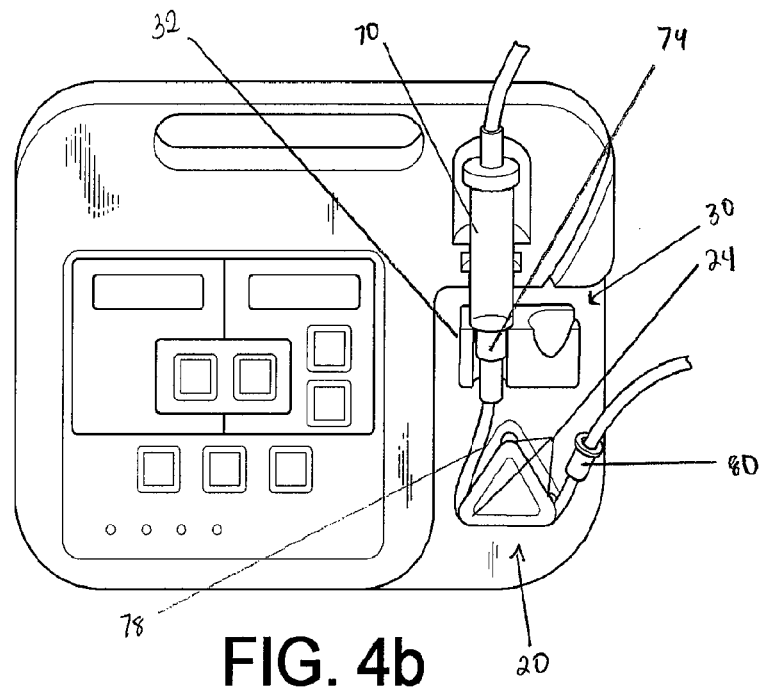

Referring now to FIG. 4b, after retaining the first medical implement 70 within the first seat 32, a user assembles the silicone tubing 78 around the pump 20 about the contact pegs 24. The proper assembling of the silicone tubing 78 will depend on the location of the pump 20 relative to the bracket 30. In the embodiment of FIG. 4b, the bracket 30 is directly above the pump 20. As a result, to assemble properly the silicone tubing 78 extending from the second chamber end 74 of the first medical implement 70, the user will wrap the silicone tubing 78 around the bottom side of the pump 20. To avoid possibly deforming or damaging the silicone tubing during this assembling step, a user should grip the second medical implement 80, or pump adapter, to stretch properly the silicone tubing 78 down and around the pump 20.

Figure 4C:
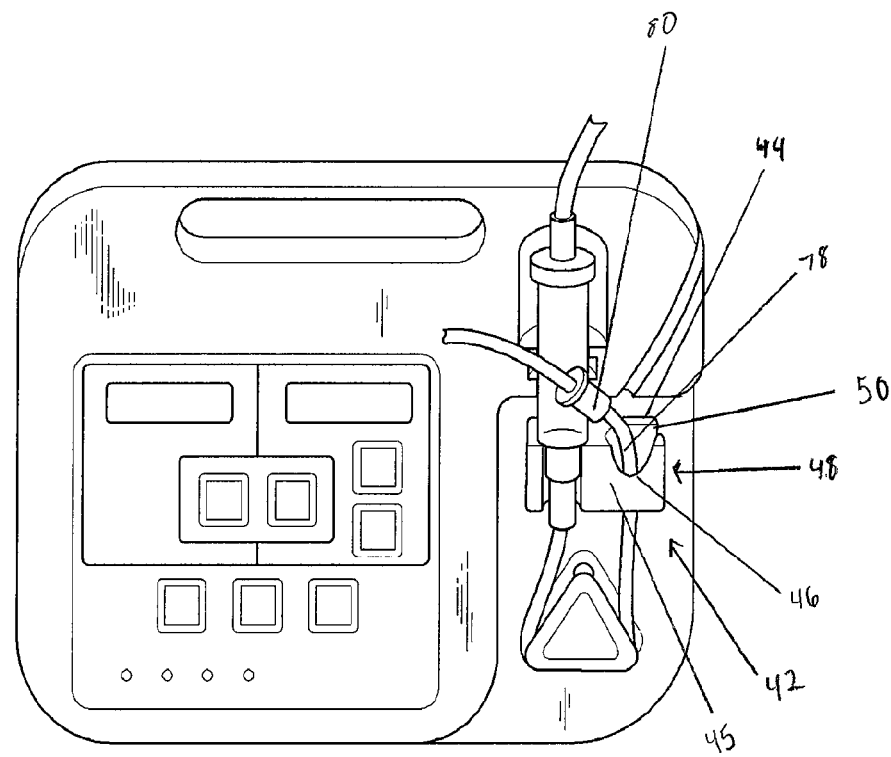

Referring now to FIG. 4c, after assembling the silicone tubing 78 about the contact pegs 24 of the pump 20, a user next affixes the second medical implement, or pump adapter, 80 onto the second seat 42 of the bracket 30. To retain properly the pump adapter 80 in the second seat 42, a user, while still grasping the pump adapter 80, lifts the pump adapter 80 above and around the bracket 30, and slides the silicone tubing 78 connected to the first adapter end 82 through the side opening 48 into the second seat 42.

As stated above and illustrated in FIG. 3b, because the side wall 54 has a larger width than the concave center surface 52, the side opening 48 has a width smaller than the width (or diameter) of the second top opening 44. Specifically, the width of the side opening 48 is sized to allow the narrow silicone tubing 78 to squeeze through the opening but not allow the wider pump adapter 80 to pass through the opening.

Next, the user inserts the pump adapter 80, at an angle, into the second seat 42 by sliding the pump adapter 80 along the concave opening 46 on the front wall 45 and through the second top opening 44. The user then returns the pump adapter 80 to a vertical alignment, allowing the pump adapter 80 to slide down into the second seat 42 and rest against the second seat ledge 50, retaining the pump adapter 80 in the second seat 42 as illustrated in FIG. 4d.

Figure 4D:
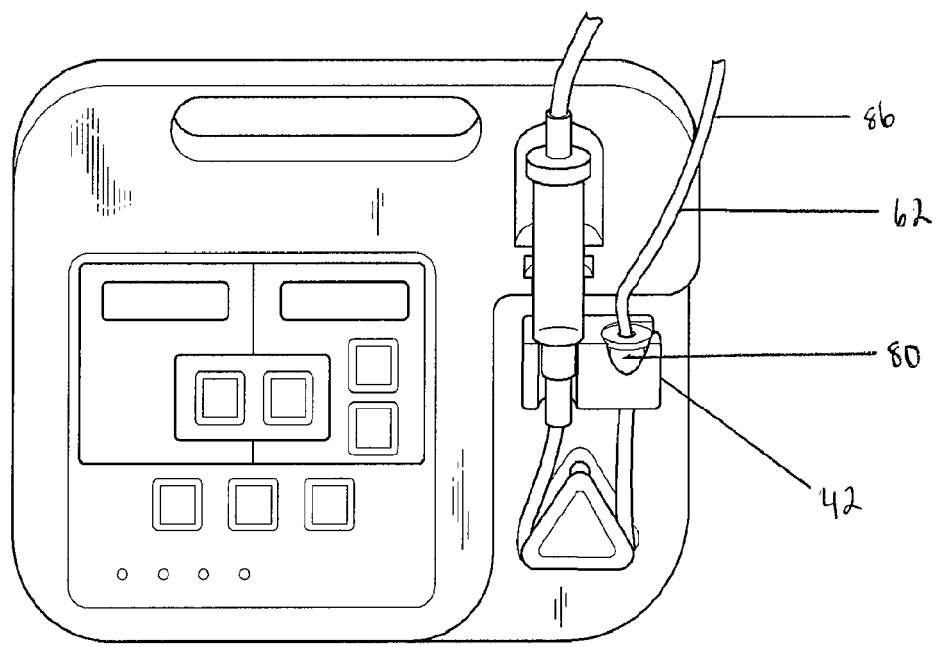

As further illustrated in FIG. 4d, after retaining the pump adapter 80 in the second seat 42, the user may further stabilize the components in and around the bracket 30 and the pump 20 by fitting the second plastic tubing 86 into the tubing guide 62. This helps prevent the second plastic tubing 86 from flailing about in response to patient movement, thereby preventing the tubing 86 from pulling upward on the adapter 80 and possibly detaching the pump adapter 80 from the second seat 42.

When retained in the second seat 42, the pump adapter 80 is not able to detach or disconnect from the bracket 30 through patient movements disruptive to the delivery system 10. Since the side opening 48 is sized to only allow insertion and removal of the silicone tubing 78, which is narrower than the pump adapter 80, the pump adapter 80 cannot detach from the bracket 30 through the side opening 48.

Moreover, unlike the front opening 36 of the first seat 32, the second seat 42 has no front opening. Instead, the front wall 45 substantially covers the front of the second seat 42. Therefore, the pump adapter 80 cannot detach from the bracket 30 through the front of the second seat 42.

Further, the pump adapter 80 rests on the second seat ledge 50 formed at the bottom of the second seat 42. Consequently, the pump adapter cannot detach from the bracket 30 through the bottom of the second seat 42. Even if the first medical implement 70 detaches from the first seat 32 and applies a downward pulling force on the pump adapter 80, the ledge 50 will prevent any further downward movement of the pump adapter 80.

Finally, because the silicone tubing 78 is taut between the first and second medical implements 70 and 80 and the second plastic tubing 86 is fitted in the tubing guide 62, minimal tubing slack exists above and below the pump adapter 80. As a result, even if the second plastic tubing 86 frees from the tubing guide 62 and is subject to tugging by patient movement, the taut assembling of the silicone tubing 78 will help prevent the pump adapter 80 from lifting off the second seat ledge 50. Regardless, even if the pump adapter 80 lifts off the second seat ledge 50, there must be sufficient force to both lift the pump adapter 80 a sufficient distance to clear the top opening 44 and concave opening 46, and also slide the silicone tubing 78 out of the second seat 42 by squeezing the silicone tubing 78 through the narrow side opening 48.

In summary, the design of the second seat 42 on the bracket 30 as described above prevents inadvertent detachment of the pump adapter 80 from the bracket 30 and, thus, prevents free flow from occurring.

With the first and second medical implements 70 and 80 secured in the bracket 30, and with the silicone tubing 78 properly assembled around the contact pegs 24 of the pump 20, the delivery apparatus 10 is ready for connection to the patient. To do so, the second plastic tubing 86 is connected to the patient or the patient's feeding tube (not shown), placing the delivery apparatus 10 in fluid communication with the patient. Using the control buttons 16A on the data input screen 14 discussed above, the user can input the appropriate settings and deliver fluid from the fluid source, through the delivery apparatus 10, and into the patient in a controlled and consistent manner using the pump as discussed above. Specifically, when activated, pump 20 will rotate counterclockwise about the rotation means 26 to occlude the silicone tubing 78 and advance medication from the drip chamber 70 to the pump adapter 80 and through the second plastic tubing 86 to the patient. Moreover, as the silicone tubing 78 opens to its natural state after compression, the pump 20 will induce fluid flow into the silicone tubing 78. Repeating this compression-expansion movement during counterclockwise rotation of the pump 20 causes controlled medication pumping through the delivery apparatus 10 to the patient.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A bracket comprising opposed front and back walls and, extending between them, opposed top and bottom walls and first and second opposed side walls:
   a first seat sized to retain a first fluid implement, the first seat extending between a first top opening in the top wall and a first bottom opening in the bottom wall, a front opening in the first seat being formed in the front wall to extend between the top and bottom walls and a first seat ledge being formed in the first seat between the top and bottom walls, a second seat sized to retain a second fluid implement, the second seat extending between a second top opening in the top wall and a second bottom opening in the bottom wall, a second seat ledge being formed in the second seat between the top and bottom walls, and a side opening in the second seat is formed in the first side wall to extend between the top and bottom walls and a concave opening in the second seat is formed in the front wall, wherein the side opening has a lesser width than the second top opening.

2. The bracket of claim 1, wherein the first seat is tapered towards a bottom opening of the first seat to retain the first fluid implement in the first seat.

3. The bracket of claim 1, wherein the bracket is affixed to a fluid delivery apparatus.

4. The bracket of claim 1, wherein the first seat further comprises a ledge positioned in the first seat to retain the first fluid implement in the first seat.

5. The bracket of claim 1, wherein the second seat further comprises a ledge positioned in the second seat to retain the second fluid implement in the second seat.

6. A bracket comprising opposed front and back walls and, extending between them, opposed top and bottom walls and first and second opposed side walls, a first seat sized to retain a first medical implement, the first seat extending between a first top opening in the top wall and a first bottom opening in the bottom wall, a front opening in the first seat being formed in the front wall to extend between the top and bottom walls and a first seat ledge being formed in the first seat between the top and bottom walls, a second seat sized to retain a second medical implement, the second seat extending between a second top opening in the top wall and a second bottom opening in the bottom wall, a second seat ledge being formed in the second seat between the top and bottom walls, and a side opening in the second seat is formed in the first side wall to extend between the top and bottom walls and a concave opening in the second seat is formed in the front wall, wherein the side opening has a lesser width than the second top opening.

7. The bracket of claim 6, wherein the first seat is tapered towards a bottom opening of the first seat to retain the first medical implement in the first scat.

8. The bracket of claim 6, wherein the bracket is affixed to a medication delivery apparatus.

9. The bracket of claim 6, wherein the first seat further comprises a ledge positioned in the first seat to retain the first medical implement in the first seat.

10. The bracket of claim 6, wherein the second seat further comprises a ledge positioned in the second seat to retain the second medical implement in the second seat.

11. A bracket comprising opposed front and back walls and, extending between them, opposed top and bottom walls and first and second opposed side walls, a first seat sized to retain a first nutritional implement, the first seat extending between a first top opening in the top wall and a first bottom opening in the bottom wall, a front opening in the first seat being formed in the front wall to extend between the top and bottom walls and a first seat ledge being formed in the first seat between the top and bottom walls, a second seat sized to retain a second nutritional implement, the second seat extending between a second top opening in the top wall and a second bottom opening in the bottom wall, a second seat ledge being formed in the second seat between the top and bottom walls, and a side opening in the second seat is formed in the first side wall to extend between the top and bottom walls and a concave opening in the second seat is formed in the front wall, wherein the side opening has a lesser width than the second top opening.

12. The bracket of claim 11, wherein the first seat is tapered towards a bottom opening of the first seat to retain the first nutritional implement in the first seat.

13. The bracket of claim 11, wherein the bracket is affixed to a nutritional delivery apparatus.

14. The bracket of claim 11, wherein the first seat further comprises a ledge positioned in the first seat to retain the first nutritional implement in the first seat.

15. The bracket of claim 11, wherein the second seat further comprises a ledge positioned in the second seat to retain the second nutritional implement in the second seat.

\* \* \* \* \*